United States Patent
Liu et al.

(10) Patent No.: US 8,178,734 B2
(45) Date of Patent: May 15, 2012

(54) PROCESSES FOR PRODUCING ETHYLENE GLYCOL FROM OXALATE(S)

(75) Inventors: Juntao Liu, Shanghai (CN); Weimin Yang, Shanghai (CN); Fengxia Sun, Shanghai (CN); Siqing Zhong, Shanghai (CN); Wanmin Wang, Shanghai (CN)

(73) Assignees: China Petroleum & Chemical Corporation, Beijing (CN); Shanghai Research Institute of Petrochemical Technology Sinopec, Shanghai (CN)

( * ) Notice: Subject to any disclaimer, the term of this patent is extended or adjusted under 35 U.S.C. 154(b) by 229 days.

(21) Appl. No.: 12/642,621

(22) Filed: Dec. 18, 2009

(65) Prior Publication Data

US 2010/0179356 A1    Jul. 15, 2010

(30) Foreign Application Priority Data

Dec. 18, 2008   (CN) .......................... 2008 1 0044133
Dec. 18, 2008   (CN) .......................... 2008 1 0044134

(51) Int. Cl.
    *C07C 27/04*   (2006.01)
(52) U.S. Cl. ...................................................... 568/864
(58) Field of Classification Search .................. 568/858, 568/864
    See application file for complete search history.

(56) References Cited

U.S. PATENT DOCUMENTS

| | | | | | |
|---|---|---|---|---|---|
| 4,112,245 | A | * | 9/1978 | Zehner et al. | 568/864 |
| 4,440,873 | A | * | 4/1984 | Miyazaki et al. | 502/244 |
| 4,453,026 | A | * | 6/1984 | Tahara et al. | 568/864 |
| 4,511,744 | A | * | 4/1985 | Miyazaki et al. | 568/864 |
| 4,551,565 | A | * | 11/1985 | Miyazaki et al. | 568/864 |
| 4,585,890 | A | * | 4/1986 | Miyazaki et al. | 560/179 |
| 4,614,728 | A | * | 9/1986 | Hirai et al. | 502/244 |
| 4,628,128 | A | * | 12/1986 | Bartley | 568/864 |
| 4,628,129 | A | * | 12/1986 | Bartley | 568/864 |
| 4,677,234 | A | * | 6/1987 | Bartley | 568/864 |
| 2006/0167323 | A1 | * | 7/2006 | Hesse et al. | 568/864 |

FOREIGN PATENT DOCUMENTS

CN    101138725 A    3/2008

OTHER PUBLICATIONS

Database CAPLUS on STN, Acc. No. 2007:475463, Zhang et al., Shiyou Huagong (2007), 36(4), p. 340-344 (abstract).*
Petroleum Chemical Industry, vol. 36, No. 4 (2007), pp. 340-343.

* cited by examiner

*Primary Examiner* — Brian J Davis
(74) *Attorney, Agent, or Firm* — Finnegan, Henderson, Farabow, Garrett & Dunner, L.L.P.

(57) ABSTRACT

Provided are processes for producing ethylene glycol from oxalate(s), wherein two or more reaction zones in series are used, and oxalate feedstock is fed stagewise, or hydrogen feedstock and optionally a solvent are fed stagewise. The present processes achieve higher selectivity for the product and improved stability of catalysts.

19 Claims, No Drawings

PROCESSES FOR PRODUCING ETHYLENE GLYCOL FROM OXALATE(S)

This application claims the benefit of Chinese Application Nos. CN200810044134.8, filed on Dec. 18, 2008 and CN200810044133.3, filed on Dec. 18, 2008.

Provided are processes for producing ethylene glycol from oxalate(s), for example, to processes for producing ethylene glycol by hydrogenating dimethyl oxalate and/or diethyl oxalate.

Ethylene glycol (EG) is an important organic chemical feedstock. It can be used in the production of polyester fibers, antifreezing agents, unsaturated polyester resin, lubricants, plasticizers, nonionic surfactants, solvents (for example, ethylene glycol ethers), explosives, etc. It also can be used in the applications of coatings, developers, brake fluids, and inks.

At present, ethylene glycol is generally produced from ethylene oxide through direct hydration process or catalytic hydration process. Another process for producing ethylene glycol is the so-called ethylene carbonate process, wherein ethylene carbonate is synthesized from ethylene oxide and carbon dioxide, and then the ethylene carbonate is hydrolyzed to form ethylene glycol. All these processes utilize petroleum as basic feedstock. Ethylene glycol also may be produced by hydrogenation of an oxalate.

Provided are processes for producing ethylene glycol from oxalate(s), comprising:

a) feeding hydrogen and a first oxalate stream to a first reaction zone to contact them with a first copper-containing catalyst under hydrogenation conditions, to form a first reaction effluent containing ethylene glycol;

b) feeding the first reaction effluent and a second oxalate stream to a second reaction zone to contact them with a second copper-containing catalyst under hydrogenation conditions, to form a second reaction effluent containing ethylene glycol; and c) isolating ethylene glycol from the second reaction effluent;

wherein the molar ratio of the oxalate(s) in the first oxalate stream to the oxalate(s) in the second oxalate stream ranges from 0.1:1 to 10:1; and wherein the molar ratio of the hydrogen to the total oxalate(s) in the first and the second oxalate streams ranges from 20:1 to 300:1.

Also provided are processes for producing ethylene glycol from oxalate(s), comprising:

a) feeding oxalate(s), a first solvent stream and a first hydrogen stream to a first reaction zone to contact them with a first copper-containing catalyst, to form a first reaction effluent containing ethylene glycol;

b) feeding the first reaction effluent, a second hydrogen stream and optionally a second solvent stream to a second reaction zone to contact them with a second copper-containing catalyst, to form a second reaction effluent containing ethylene glycol; and c) isolating ethylene glycol from the second reaction effluent;

wherein the first and the second solvent streams are independently selected from $C_1$ to $C_5$ alcohols, $C_2$ to $C_{10}$ ethers, $C_5$ to $C_{10}$ alkanes, $C_5$ to $C_{10}$ cycloalkanes, $C_6$ to $C_{10}$ aromatic hydrocarbons, and mixtures thereof; the molar ratio of the first solvent stream to the second solvent stream is at least 0.1:1; the molar ratio of the first hydrogen stream to the second hydrogen stream ranges from 0.2:1 to 10:1; and the molar ratio of the oxalate(s) to the total hydrogen in the first and the second hydrogen streams to the total solvent in the first and the second solvent streams is 1:30 to 200:0.1 to 5.

Provided are processes for producing ethylene glycol from oxalate(s) (referred to as the first process hereinafter), comprising:

a) feeding hydrogen and a first oxalate stream to a first reaction zone to contact them with a first copper-containing catalyst under hydrogenation conditions, to form a first reaction effluent containing ethylene glycol;

b) feeding the first reaction effluent and a second oxalate stream to a second reaction zone to contact them with a second copper-containing catalyst under hydrogenation conditions, to form a second reaction effluent containing ethylene glycol; and c) isolating ethylene glycol from the second reaction effluent;

wherein the molar ratio of the oxalate(s) in the first oxalate stream to the oxalate(s) in the second oxalate stream ranges from 0.1:1 to 10:1; and wherein the molar ratio of the hydrogen to the total oxalate(s) in the first and the second oxalate streams ranges from 20:1 to 300:1.

In some embodiments, the oxalate(s) useful for the first process may be selected from dimethyl oxalate, diethyl oxalate, dipropyl oxalate, diisopropyl oxalate, and mixtures thereof. In some embodiments, the oxalate(s) may be diluted with a solvent such as a $C_1$-$C_5$ alcohol, a $C_2$-$C_{10}$ ether, a $C_5$-$C_{10}$ alkane, a $C_5$-$C_{10}$ cycloalkane, or a $C_6$-$C_{10}$ aromatic hydrocarbon. In some embodiments, the solvent may be used in such an amount that the molar ratio of the solvent to the total oxalate(s) ranges from 0.1:1 to 5:1. The solvent and the oxalate(s) may be fed in an admixture or separately. In some embodiments, the introduction of the solvent may help to reduce adiabatic temperature rise at the active sites of the catalyst.

In some embodiments of the first process, the first reaction zone is operated at a reaction temperature ranging from 100 to 260° C., for example, from 130 to 230° C. In some embodiments of the first process, the first reaction zone is operated at a WHSV ranging from 0.05 to 10 $h^{-1}$, for example, from 0.08 to 6 $h^{-1}$. In some embodiments of the first process, the first reaction zone is operated at a hydrogen/oxalate(s) molar ratio ranging from 30:1 to 200:1, for example, from 40:1 to 150:1. In some embodiments of the first process, the first reaction zone is operated at a reaction pressure ranging from 0.2 to 5.0 MPa (absolute, the same below), for example, from 0.5 to 3.0 MPa.

In some embodiments of the first process, the first reaction zone is operated under the following conditions:

a reaction temperature ranging from 100 to 260° C., for example, from 130 to 230° C.; a WHSV ranging from 0.05 to 10 $h^{-1}$, for example, from 0.08 to 6 $h^{-1}$; a hydrogen/oxalate(s) molar ratio ranging from 30:1 to 200:1, for example, from 40:1 to 150:1; and a reaction pressure ranging from 0.2 to 5.0 MPa (absolute, the same below), for example, from 0.5 to 3.0 MPa.

In some embodiments of the first process, the second reaction zone is operated at a reaction temperature ranging from 180 to 300° C., for example, from 180 to 260° C. In some embodiments of the first process, the second reaction zone is operated at a WHSV ranging from 0.08 to 8 $h^{-1}$, for example, from 0.1 to 5 $h^{-1}$. In some embodiments of the first process, the second reaction zone is operated at a reaction pressure ranging from 1.0 to 10.0 MPa, for example, from 1.5 to 6.0 MPa.

In some embodiments of the first process, the second reaction zone is operated at a reaction temperature ranging from 180 to 300° C., for example, from 180 to 260° C.; a WHSV ranging from 0.08 to 8 $h^{-1}$, for example, from 0.1 to 5 $h^{-1}$; and a reaction pressure ranging from 1.0 to 10.0 MPa, for example, from 1.5 to 6.0 MPa.

In some embodiments of the first process, the molar ratio of the oxalate(s) in the first oxalate stream to the oxalate(s) in the second oxalate stream ranges from 0.2:1 to 8:1, for example, from 0.3:1 to 6:1.

In some embodiments of the first process, the first reaction zone is operated under the following conditions:

a reaction temperature ranging from 100 to 260° C., for example, from 130 to 230° C.; a WHSV ranging from 0.05 to 10 $h^{-1}$, for example, from 0.08 to 6 $h^{-1}$; a hydrogen/oxalate(s) molar ratio ranging from 30:1 to 200:1, for example, from 40:1 to 150:1; and a reaction pressure ranging from 0.2 to 5.0 MPa (absolute, the same below), for example, from 0.5 to 3.0 MPa;

the second reaction zone is operated under the following conditions: a reaction temperature ranging from 180 to 300° C., for example, from 180 to 260° C.; a WHSV ranging from 0.08 to 8 $h^{-1}$, for example, from 0.1 to 5 $h^{-1}$; and a reaction pressure ranging from 1.0 to 10.0 MPa, for example, from 1.5 to 6.0 MPa; and the molar ratio of the oxalate(s) in the first oxalate stream to the oxalate(s) in the second oxalate stream ranges from 0.2:1 to 8:1, for example, from 0.3:1 to 6:1.

In some embodiments of the first process, the reaction temperature in the second reaction zone may be higher than the reaction temperature in the first reaction zone by at least 10° C., for example, by at least 20° C., or for another example, by at least 30° C.

In some embodiments, the copper-containing catalysts used in the first process comprise an active component, a carrier and an optional assistant. In some embodiments, the carrier comprises silica, alumina, or both. In some embodiments, the active component may be selected from metal copper, oxides of copper, and mixtures thereof, and the content of the active component ranges from 0.02 to 60 wt %, for example, from 0.1 to 50 wt %, based on weight of the catalyst. In some embodiments, the assistant comprises at least one metal selected from zinc, manganese, barium, chromium, nickel and iron, or oxides thereof, and the content of the assistant ranges from 0 to 30 wt %, for example, from 0.5 to 20 wt %, based on weight of the catalyst.

In some embodiments, the ethylene glycol may be separated from the second reaction effluent by a process known in the art.

Additionally, it will be understood by those skilled in the art that, in some embodiments, the first process may employ three or more reaction zones. If three or more reaction zones are used, the effluent from a preceding reaction zone, after complemented with an oxalate feedstock, may be fed to the next reaction zone, ethylene glycol product is separated from the effluent of the last reaction zone, and the third and later reaction zones may be operated under conditions similar to those employed in the second reaction zone.

As described above, in some embodiments, the first process is performed in a manner wherein at least two reaction zones in series are used, the feedstock is fed stagewise, the first reaction zone is operated at a lower temperature, and the second reaction zone and the possible subsequent reaction zone(s) are operated at a higher temperature. Hydrogenation of an oxalate is an exothermal reaction. Without limited by a specific theory, it is believed that a main cause deactivating a catalyst used in hydrogenation of an oxalate is the coking on the catalyst and the sintering of the grains of the active component. Concentrative exotherm during hydrogenation may result in a higher temperature rise in the catalyst, for example, at the catalytic active sites, wherein the temperature at the catalytic active sites may be higher than the apparent temperature of the catalyst by tens or even more than one hundred degrees Celsius. An over high local temperature rise may seriously affect the lifetime of the catalyst, because it may not only greatly accelerate the coking reaction on the catalyst but also may accelerate the growth of the grains, thereby accelerating the deactivation of the catalyst and shortening the regeneration period of the catalyst. It is also believed that hydrogenation of an oxalate is a typical series reaction, and an intermediate product can be advantageously formed at a lower temperature, and then converted into the target product, ethylene glycol, at a higher temperature. In the first process, the stagewise addition of the feedstock and the lower-temperature operation of the first reaction zone may alleviate concentrative exotherm of the hydrogenation, may optimize thermal management of the reaction process, and may avoid quick deactivation of the catalyst caused by an over high local temperature rise, and the higher-temperature operation of the second reaction zone may ensure that the intermediate product formed in the first reaction zone may be more fully converted into the target product, ethylene glycol, thereby enhancing the yield of and the selectivity for the target product, ethylene glycol.

In some embodiments of the first process, dimethyl oxalate as feedstock is hydrogenated in the presence of a copper-containing catalyst described above under the following conditions:

operation conditions of the first reaction zone: a reaction temperature ranging from 130 to 230° C., a WHSV ranging from 0.08 to 6 $h^{-1}$, a molar ratio of hydrogen to the oxalates ranging from 40:1 to 150:1, and a reaction pressure ranging from 0.5 to 3.0 MPa;

operation conditions of the second reaction zone: a reaction temperature ranging from 180 to 260° C., a WHSV ranging from 0.1 to 5 $h^{-1}$, and a reaction pressure ranging from 1.5 to 6.0 MPa;

a molar ratio of the oxalates in the first oxalate stream to the oxalates in the second oxalate stream ranging from 0.3:1 to 6:1; and a molar ratio of the hydrogen to the total oxalates in the first and the second oxalate streams ranging from 20:1 to 300:1.

In some embodiments, a conversion of dimethyl oxalate of greater than 98% and a selectivity for ethylene glycol of greater than 85% may be achieved.

Also provided are processes for producing ethylene glycol from oxalate(s) (referred to as the second process hereinafter), comprising:

a) feeding oxalate(s), a first solvent stream and a first hydrogen stream to a first reaction zone to contact them with a first copper-containing catalyst, to form a first reaction effluent containing ethylene glycol;

b) feeding the first reaction effluent, a second hydrogen stream and optionally a second solvent stream to a second reaction zone to contact them with a second copper-containing catalyst, to form a second reaction effluent containing ethylene glycol; and c) isolating ethylene glycol from the second reaction effluent;

wherein, the first and the second solvent streams are independently selected from $C_1$ to $C_5$ alcohols, $C_2$ to $C_{10}$ ethers, $C_5$ to $C_{10}$ alkanes, $C_5$ to $C_{10}$ cycloalkanes, $C_6$ to $C_{10}$ aromatic hydrocarbons, and mixtures thereof;

the molar ratio of the first solvent stream to the second solvent stream ranges from at least 0.1:1, for example, from 0.1:1 to 10:1, for another example, from 0.2:1 to 8:1, and yet for another example, from 0.3:1 to 6:1;

the molar ratio of the first hydrogen stream to the second hydrogen stream ranges from 0.2:1 to 10:1, for example, from 0.3:1 to 8:1, and for another example, from 0.5:1 to 7:1; and the molar ratio of the oxalate(s) to the total hydrogen in the first and the second hydrogen streams to the total solvent in the first and the second solvent streams ranges from 1:30 to 200:0.1 to 5.

In some embodiments of the second process, the first and the second solvent streams are independently selected from methanol, ethanol, propanol, cyclohexane, and mixtures thereof. In some embodiments, the first and the second solvent streams are independently selected from methanol, ethanol, and mixtures thereof.

In some embodiments, of the second process, the first reaction zone is operated at a reaction temperature ranging from 100 to 260° C., for example, from 130 to 230° C. In some embodiments, of the second process, the first reaction zone is operated at a WHSV ranging from 0.05 to 10 $h^{-1}$, for example, from 0.08 to 6 $h^{-1}$. In some embodiments, of the second process, the first reaction zone is operated at a reaction pressure ranging from 0.2 to 5.0 MPa, for example, from 0.5 to 4.0 MPa. In some embodiments, of the second process, the first reaction zone is operated at a mass fraction of the oxalate (s) ranging from 0.5 to 95%, for example, from 1.0 to 60%, based on the total feed.

In some embodiments, of the second process, the first reaction zone is operated under at a reaction temperature ranging from 100 to 260° C., for example, from 130 to 230° C.; a WHSV ranging from 0.05 to 10 $h^{-1}$, for example, from 0.08 to 6 $h^{-1}$; a reaction pressure ranging from 0.2 to 5.0 MPa, for example, from 0.5 to 4.0 MPa; and a mass fraction of the oxalate(s) ranging from 0.5 to 95%, for example, from 1.0 to 60%, based on the total feed.

In some embodiments, of the second process, the second reaction zone is operated at a reaction temperature ranging from 180 to 300° C., for example, from 180 to 260° C. In some embodiments, of the second process, the second reaction zone is operated at a WHSV ranging from 0.08 to 8 $h^{-1}$, for example, from 0.1 to 5 $h^{-1}$. In some embodiments, of the second process, the second reaction zone is operated at a reaction pressure ranging from 1.0 to 10.0 MPa, for example, from 1.5 to 6.0 MPa. In some embodiments, of the second process, the second reaction zone is operated at a reaction temperature ranging from 180 to 300° C., for example, from 180 to 260° C.; a WHSV ranging from 0.08 to 8 $h^{-1}$, for example, from 0.1 to 5 $h^{-1}$; and a reaction pressure ranging from 1.0 to 10.0 MPa, for example, from 1.5 to 6.0 MPa.

In some embodiments, of the second process, the first reaction zone is operated under the following conditions:

a reaction temperature ranging from 100 to 260° C., for example, from 130 to 230° C.; a WHSV ranging from 0.05 to 10 $h^{-1}$, for example, from 0.08 to 6 $h^{-1}$; a reaction pressure ranging from 0.2 to 5.0 MPa, for example, from 0.5 to 4.0 MPa; and a mass fraction of the oxalate(s) ranging from 0.5 to 95%, for example, from 1.0 to 60%, based on the total feed; and the second reaction zone is operated under the following conditions: a reaction temperature ranging from 180 to 300° C., for example, from 180 to 260° C.; a WHSV ranging from 0.08 to 8 $h^{-1}$, for example, from 0.1 to 5 $h^{-1}$; and a reaction pressure ranging from 1.0 to 10.0 MPa, for example, from 1.5 to 6.0 MPa.

In some embodiments of the second process, the reaction temperature in the second reaction zone is higher than the reaction temperature in the first reaction zone by at least 10° C., for example, by at least 20° C., and for another example, by at least 30° C.

In some embodiments of the second process, the oxalate(s) may be selected from dimethyl oxalate, diethyl oxalate, dipropyl oxalate, diisopropyl oxalate, and mixtures thereof.

In some embodiments of the second process, the copper-containing catalysts may be those described for the first process.

In some embodiments of the second process, the ethylene glycol may be separated from the second reaction effluent by a process known in the art.

Additionally, it will be understood by those skilled in the art that, in some embodiments, the second process may employ three or more reaction zones. If three or more reaction zones are used, the effluent from a preceding reaction zone, after complemented with hydrogen and optionally with a solvent, is fed to the next reaction zone, ethylene glycol product is separated from the effluent of the last reaction zone, and the third and the later reaction zone(s) may be operated under conditions similar to those employed in the second reaction zone.

As described above, in some embodiments, the second process is performed in a manner wherein at least two reaction zones in series are used, hydrogen is fed stagewise, and a solvent is added at least to the first reaction zone. The hydrogenation of an oxalate is an exothermal reaction. Without limited by a specific theory, it is believed that a main cause deactivating a catalyst used in hydrogenation of an oxalate is the coking on the catalyst and the sintering of the grains of the active component. Concentrative exotherm during hydrogenation may result in a higher temperature rise in the catalyst, for example, at the catalytic active sites, wherein the temperature at the catalytic active sites may be higher than the apparent temperature of the catalyst by tens or even more than one hundred degrees Celsius. Over high local temperature rise may seriously influence the lifetime of the catalyst, because it not only greatly accelerates the coking reaction on the catalyst but also accelerates the growth of the grains, thereby accelerating the deactivation of the catalyst and shortening the regeneration period of the catalyst. In some embodiments, the second process employs reaction zones in series, the stagewise addition of the hydrogen, and the addition of the solvent at least to the first reaction zone. The above means may alleviate the exotherm of the hydrogenation, and may help to avoid an over high local temperature rise in the catalyst, thereby effectively maintaining the performance of the catalyst and prolonging the lifetime of the catalyst. It is also believed that hydrogenation of an oxalate is a series reaction, and the target product, ethylene glycol, may be further hydrogenated to form ethanol. The larger the hydrogen/oxalate ratio (i.e., the molar ratio of the hydrogen to the oxalate), the larger the probability of the formation of ethanol. In some embodiments of the second process, the stagewise addition of hydrogen provides a suitable hydrogen/oxalate ratio required by the hydrogenation of the oxalate to form ethylene glycol and, at the same time, favors the reduction of side reactions producing ethanol, thereby enhancing the yield of and the selectivity for the target product, ethylene glycol.

In some embodiments of the second process, dimethyl oxalate as feedstock is hydrogenated in the presence of a copper-containing catalyst described above under the following conditions:

operation conditions of the first reaction zone: a reaction temperature ranging from 130 to 230° C., a WHSV ranging from 0.08 to 6 $h^{-1}$, a reaction pressure ranging from 0.5 to 4.0 MPa, and a mass fraction of the oxalate ranging from 1.0 to 60%;

operation conditions of the second reaction zone: a reaction temperature ranging from 180 to 260° C., a WHSV ranging from 0.1 to 5 h$^{-1}$, and a reaction pressure ranging from 1.5 to 6.0 MPa;

a molar ratio of the first solvent stream to the second solvent ranging from 0.3:1 to 6:1, with the first and the second solvent streams being independently methanol and/or ethanol;

a molar ratio of the first hydrogen stream to the second hydrogen stream ranging from 0.5:1 to 7:1; and a molar ratio of the dimethyl oxalate feedstock to the total hydrogen in the first and the second hydrogen streams to the total solvent in the first and the second solvent streams ranging 1:30 to 200:0.1 to 5.

In some embodiments, a conversion of dimethyl oxalate of greater than 98% and a selectivity for ethylene glycol of greater than 85% may be achieved.

EXAMPLES

The following examples are given for further illustrating the invention, without limiting the invention in any way.

Example 1

A 25% CuO/SiO$_2$ catalyst precursor (25 wt %, based on SiO$_2$ carrier, of CuO supported on the SiO$_2$ carrier, similarly below) was prepared as follows: 59 g of copper nitrate was dissolved in 300 ml of water to prepare an impregnation solution. 100 g of a silica carrier having a specific surface area of 200 m$^2$/g was impregnated with the solution for 20 hours, and then dried at room temperature under vacuum for 8 hours to obtain solids. The solids was further dried at 120° C. for 10 hours, and then calcined at 500° C. for 6 hours, to obtain the desired 25% CuO/SiO$_2$ catalyst precursor.

80 g of the above prepared 25 wt % CuO/SiO$_2$ catalyst precursor was split equally into two portions, which were loaded into a first tubular reactor and a second tubular reactor, respectively, both reactors having a diameter of 18 mm. The catalyst precursor in the two reactors was heated from room temperature to 450° C. at a rate of 3° C./min under a mixed gas flow (having a hydrogen content of 20 mol % and a nitrogen content of 80 mol %) of 100 mL/min, and maintained at 450° C. for 4 hours to be activated, to form a first copper-containing catalyst and a second copper-containing catalyst having the same composition.

This example used hydrogen and dimethyl oxalate as feedstock, wherein the dimethyl oxalate was split into a first feedstock stream and a second feedstock stream, the molar ratio of the first feedstock stream to the second feedstock stream was 0.5:1, and the molar ratio of the hydrogen to the total dimethyl oxalate was 100:1. The hydrogen and the first feedstock stream were fed to the first reactor to contact with the first copper-containing catalyst, to form a first reaction effluent containing ethylene glycol. Then the first reaction effluent and the second feedstock stream were fed to the second reactor to contact with the second copper-containing catalyst, to form a second reaction effluent containing ethylene glycol. The first reactor was operated under the following conditions: a reaction temperature of 150° C., a WHSV of 0.1 hr$^{-1}$, and a reaction pressure of 0.5 MPa; and the second reactor was operated under the following conditions: a reaction temperature of 230° C., a WHSV of 0.2 hr$^{-1}$, and a reaction pressure of 3.5 MPa. Upon the run was stable (after about 20 hours), reaction results were obtained as follows: conversion of dimethyl oxalate was 96.7%, and selectivity for ethylene glycol was 87.4%.

Example 2

Cu—Cu$_2$O—Zn/SiO$_2$ catalyst I having a composition of 35% Cu+10% Cu$_2$O+5% Zn on SiO$_2$ and Cu—Cu$_2$O/Al$_2$O$_3$ catalyst II having a composition of 20% Cu+5% Cu$_2$O on Al$_2$O$_3$ were prepared according to a procedure similar to that described in Example 1.

This example used hydrogen and dimethyl oxalate as feedstock, wherein the dimethyl oxalate was split into a first feedstock stream and a second feedstock stream, the molar ratio of the first feedstock stream to the second feedstock stream was 1:1, and the molar ratio of the hydrogen to the total dimethyl oxalate was 60:1. The hydrogen and the first feedstock stream were fed to the first reactor to contact with the copper-containing catalyst I, to form a first reaction effluent containing ethylene glycol. The first reaction effluent and the second feedstock stream were fed to the second reactor to contact with the copper-containing catalyst II, to form a second reaction effluent containing ethylene glycol. The first reactor was operated under the following conditions: a reaction temperature of 140° C., a WHSV of 0.2 hr$^{-1}$, and a reaction pressure of 0.5 MPa; and the second reactor was operated under the following conditions: a reaction temperature of 190° C., a WHSV of 0.3 hr$^{-1}$, and a reaction pressure of 3.5 MPa. Reaction results were obtained as follows: conversion of dimethyl oxalate was 98.8%, and selectivity for ethylene glycol was 83.1%.

Example 3

Cu—Cu$_2$O—Fe$_2$O$_3$/SiO$_2$ catalyst I having a composition of 48% Cu+2% Cu$_2$O+5% Fe$_2$O$_3$ on SiO$_2$ and Cu—Cu$_2$O/Al$_2$O$_3$ catalyst II having a composition of 40% Cu+20% Cu$_2$O/Al$_2$O$_3$ were prepared according to a procedure similar to that described in Example 1.

This example used hydrogen and oxalate as feedstock, wherein the oxalate is a 1:1 by mole mixture of dimethyl oxalate and diethyl oxalate, the oxalate feedstock was split into a first feedstock stream and a second feedstock stream, the molar ratio of the first feedstock stream to the second feedstock stream was 3:1, and the molar ratio of the hydrogen to the total oxalate feedstock was 160:1. The hydrogen and the first feedstock stream were fed to the first reactor to contact with the copper-containing catalyst I, to form a first reaction effluent containing ethylene glycol. The first reaction effluent and the second feedstock stream were fed to the second reactor to contact with the copper-containing catalyst II, to form a second reaction effluent containing ethylene glycol. The first reactor was operated under the following conditions: a reaction temperature of 180° C., a WHSV of 1 hr$^{-1}$, and a reaction pressure of 1.5 MPa; and the second reactor was operated under the following conditions: a reaction temperature of 230° C., a WHSV of 0.9 hr$^{-1}$, and a reaction pressure of 1.8 MPa. Reaction results were obtained as follows: conversion of the oxalate was 100%, and selectivity for ethylene glycol was 90.3%.

Example 4

CuO—Cu$_2$O—BaO/SiO$_2$ catalyst I having a composition of 6% CuO+3% Cu$_2$O+5% BaO on SiO$_2$ and CuO—Cu$_2$O—Cr$_2$O$_3$/SiO$_2$ catalyst II having a composition of 20% Cu+8% Cu$_2$O+30% Cr$_2$O$_3$ on SiO$_2$ were prepared according to a procedure similar to that described in Example 1.

This example used hydrogen and oxalate as feedstock, wherein the oxalate is a 2:1 by mole mixture of dimethyl oxalate and diethyl oxalate, the oxalate feedstock was split into a first feedstock stream and a second feedstock stream, the molar ratio of the first feedstock stream to the second feedstock stream was 8:1, and the molar ratio of the hydrogen to the total oxalate was 200:1. The hydrogen and the first feedstock stream were fed to the first reactor to contact with the copper-containing catalyst I, to form a first reaction effluent containing ethylene glycol. The first reaction effluent and the second feedstock stream were fed to the second reactor to contact with the copper-containing catalyst II, to form a second reaction effluent containing ethylene glycol. The first reactor was operated under the following conditions: a reaction temperature of 200° C., a WHSV of 3 hr$^{-1}$, and a reaction pressure of 2.2 MPa; and the second reactor was operated under the following conditions: a reaction temperature of 240° C., a WHSV of 2.5 hr$^{-1}$, and a reaction pressure of 2.2 MPa. Reaction results were obtained as follows: conversion of the oxalate was 100%, and selectivity for ethylene glycol was 92.3%.

Example 5

CuO—Cu$_2$O—ZnO/SiO$_2$ catalyst I having a composition of 10% CuO+3% Cu$_2$O+10% ZnO on SiO$_2$ and CuO—Cu$_2$O—Cr$_2$O$_3$—MnO/SiO$_2$ catalyst II having a composition of 20% CuO+8% Cu$_2$O+30% Cr$_2$O$_3$+2% MnO on SiO$_2$ were prepared according to a procedure similar to that described in Example 1

This example used hydrogen and oxalate as feedstock, wherein the oxalate feedstock included a first feedstock stream consisting of dimethyl oxalate and a second feedstock stream consisting of diethyl oxalate, the molar ratio of the first feedstock stream to the second feedstock stream was 8:1, and the molar ratio of the hydrogen to the total oxalate was 200:1. The hydrogen and the first feedstock stream were fed to the first reactor to contact with the copper-containing catalyst I, to form a first reaction effluent containing ethylene glycol. The first reaction effluent and the second feedstock stream were fed to the second reactor to contact with the copper-containing catalyst II, to form a second reaction effluent containing ethylene glycol. The first reactor was operated under the following conditions: a reaction temperature of 210° C., a WHSV of 5 hr$^{-1}$, and a reaction pressure of 3.5 MPa; and the second reactor was operated under the following conditions: a reaction temperature of 250° C., a WHSV of 5 hr$^{-1}$, and a reaction pressure of 3.5 MPa. Reaction results were obtained as follows: conversion of the oxalate was 100%, and selectivity for ethylene glycol was 94.6%.

Example 6

CuO—Cu—Cu$_2$O—ZnO/SiO$_2$ catalyst I having a composition of 35% CuO+5% Cu+10% Cu$_2$O+25% ZnO on SiO$_2$, CuO—Cu—Cu$_2$O/Al$_2$O$_3$ catalyst II having a composition of 20% CuO+10% Cu+5% Cu$_2$O on Al$_2$O$_3$, and CuO—Cu$_2$O—Cr$_2$O$_3$/Al$_2$O$_3$ catalyst III having a composition of 10% CuO+15% Cu$_2$O+10% Cr$_2$O$_3$ on Al$_2$O$_3$ were prepared according to a procedure similar to that described in Example 1.

This example used hydrogen and dimethyl oxalate as feedstock, wherein the dimethyl oxalate feedstock was split into a first feedstock stream, a second feedstock stream, and a third feedstock stream, the molar ratio of the first feedstock stream to the second feedstock stream to the third feedstock stream was 1:1:1.5, and the molar ratio of the hydrogen to the total dimethyl oxalate was 80:1. The hydrogen and the first feedstock stream were fed to the first reactor to contact with the copper-containing catalyst I, to form a first reaction effluent containing ethylene glycol. The first reaction effluent and the second feedstock stream were fed to the second reactor to contact with the copper-containing catalyst II, to form a second reaction effluent containing ethylene glycol. The second reaction effluent and the third feedstock stream were fed to the third reactor to contact with the copper-containing catalyst III, to form a third reaction effluent containing ethylene glycol. The first reactor was operated under the following conditions: a reaction temperature of 230° C., a WHSV of 0.8 hr$^{-1}$, and a reaction pressure of 6 MPa; the second reactor was operated under the following conditions: a reaction temperature of 240° C., a WHSV of 3 hr$^{-1}$, and a reaction pressure of 6 MPa; and the third reactor was operated under the following conditions: a reaction temperature of 250° C., a WHSV of 2 hr$^{-1}$, and a reaction pressure of 6 MPa. Reaction results were obtained as follows: conversion of dimethyl oxalate was 100%, and selectivity for ethylene glycol was 97.3%.

Comparative Example 1

CuO—Cu$_2$O—BaO/SiO$_2$ catalyst I having a composition of 6% CuO+3% Cu$_2$O+5% BaO on SiO$_2$ was prepared according to a procedure similar to that described in Example 1.

This example used hydrogen and oxalate as feedstock, wherein the oxalate is a 2:1 by mole mixture of dimethyl oxalate and diethyl oxalate, and the molar ratio of the hydrogen to the total oxalate was 200:1. The hydrogen and the oxalate as feedstock were fed to the reactor to contact with the copper-containing catalyst I contained therein, to form a reaction effluent containing ethylene glycol. The reactor was operated under the following conditions: a reaction temperature of 200° C., a WHSV of 1.36 hr$^{-1}$, and a reaction pressure of 2.2 MPa.

Comparison of the reaction results obtained in Example 4 and Comparative Example 1 is shown in the Table 1 below.

TABLE 1

Comparison of reaction results obtained from a two-reactors-in-series process (as described herein) and from a one-stage-reactor process

| Two-reactors-in-series process (Example 4) | | | One-stage reactor process (Comp. Example 1) | | |
|---|---|---|---|---|---|
| Time, hours | Oxalate conversion, % | Selectivity for ethylene glycol, % | Time, hours | Oxalate conversion, % | Selectivity for ethylene glycol, % |
| 7.2 | 100 | 90.90 | 7.2 | 85.7 | 52.50 |
| 12 | 100 | 86.86 | 12 | 98.8 | 84.53 |
| 30.6 | 99.5 | 91.29 | 30.6 | 99.5 | 86.90 |
| 40.2 | 99 | 91.72 | 40.2 | 95.3 | 84.65 |
| 41.4 | 100 | 91.29 | 41.4 | 91.2 | 81.90 |
| 54 | 99 | 92.12 | 54 | 85 | 78.75 |
| 60 | 98.8 | 92.30 | 60 | 75 | 70.35 |
| 69.6 | 100 | 91.01 | 69.6 | 50 | 52.50 |
| 109.2 | 100 | 91.38 | | | |
| 144.6 | 99.8 | 89.05 | | | |
| 312.6 | 100 | 90.03 | | | |
| 422.4 | 100 | 90.57 | | | |
| 810 | 100 | 88.43 | | | |
| 936 | 100 | 90.63 | | | |

From the data shown in the above table, it can be seen that the processes described herein are superior to the conventional technical solution with respect to the conversion of the feedstock, the selectivity for the product, and the stability of the catalyst.

Example 7

A 25% CuO/SiO$_2$ catalyst precursor was prepared as follows: 35.5 g of copper nitrate was dissolved in 180 ml of water to prepare an impregnation solution. 60 g of a silica carrier having a specific surface area of 250 m²/g was impregnated with the solution for 20 hours, and then dried at room temperature under vacuum for 8 hours to obtain solids. The solids was further dried at 120° C. for 10 hours, and then calcined at 500° C. for 6 hours, to obtain the desired 25% $CuO/SiO_2$ catalyst precursor.

The above prepared 25% $CuO/SiO_2$ catalyst precursor was split equally into two portions, which were loaded into a first tubular reactor and a second tubular reactor, respectively, both reactors having a diameter of 18 mm. The catalyst precursor in the two reactors was heated from room temperature to 450° C. at a rate of 2° C./min under a mixed gas flow (having a hydrogen content of 20 mol % and a nitrogen content of 80 mol %) of 100 mL/min, and maintained at 450° C. for 6 hours to be activated, to form a first copper-containing catalyst and a second copper-containing catalyst having the same composition.

This example used dimethyl oxalate and hydrogen as feedstock, and methanol as solvent, wherein the molar ratio of the dimethyl oxalate to the hydrogen to the solvent was 1:80:2, the hydrogen feedstock was split into a first hydrogen stream and a second hydrogen stream in a molar ratio of 0.5:1, and the methanol solvent was split into a first solvent stream and a second solvent stream in a molar ratio of 0.5:1. The dimethyl oxalate, the first hydrogen stream and the first solvent stream were fed to the first reactor to contact with the first copper-containing catalyst, to form a first reaction effluent containing ethylene glycol. The first reaction effluent, the second solvent stream and the second hydrogen stream were fed to the second reactor to contact with the second copper-containing catalyst, to form a second reaction effluent containing ethylene glycol. The first reactor was operated under the following conditions: a reaction temperature of 150° C., a WHSV of 0.1 $h^{-1}$, and a reaction pressure of 0.5 MPa; and the second reactor was operated under the following conditions: a reaction temperature of 230° C., a WHSV of 0.2 $hr^{-1}$, and a reaction pressure of 3.5 MPa. Reaction results were obtained as follows: conversion of dimethyl oxalate was 95.4%, and selectivity for ethylene glycol was 89.7%.

Example 8

$CuO/SiO_2$ catalyst I having a composition of 35% $CuO/SiO_2$ and $CuO/SiO_2$ catalyst II having a composition of 50% $CuO/SiO_2$ were prepared according to a procedure similar to that described in Example 7.

This example used dimethyl oxalate and hydrogen as feedstock, and methanol as solvent, wherein the molar ratio of the dimethyl oxalate to the hydrogen to the solvent was 1:150:1, the hydrogen feedstock was split into a first hydrogen stream and a second hydrogen stream in a molar ratio of 1:1, and the methanol solvent was split into a first solvent stream and a second solvent stream in a molar ratio of 1:1. The dimethyl oxalate, the first hydrogen stream and the first solvent stream were fed to the first reactor to contact with the copper-containing catalyst I, to form a first reaction effluent containing ethylene glycol. The first reaction effluent, the second solvent stream and the second hydrogen stream were fed to the second reactor to contact with the copper-containing catalyst II, to form a second reaction effluent containing ethylene glycol. The first reactor was operated under the following conditions: a reaction temperature of 130° C., a WHSV of 0.2 $hr^{-1}$, and a reaction pressure of 0.5 MPa; and the second reactor was operated under the following conditions: a reaction temperature of 190° C., a WHSV of 0.3 $hr^{-1}$, and a reaction pressure of 3.5 MPa. Reaction results were obtained as follows: conversion of dimethyl oxalate was 98.3%, and selectivity for ethylene glycol was 84.5%.

Example 9

$CuO/SiO_2$ catalyst I having a composition of 15% $CuO/SiO_2$ and $CuO/SiO_2$ catalyst II having a composition of 60% $CuO/SiO_2$ were prepared according to a procedure similar to that described in Example 7.

This example used diethyl oxalate and hydrogen as feedstock, and ethanol as solvent, wherein the molar ratio of the diethyl oxalate to the hydrogen to the solvent was 1:250:1, the hydrogen feedstock was split into a first hydrogen stream and a second hydrogen stream in a molar ratio of 2:1, and the ethanol solvent was split into a first solvent stream and a second solvent stream in a molar ratio of 3:1. The diethyl oxalate, the first hydrogen stream and the first solvent stream were fed to the first reactor to contact with the copper-containing catalyst I, to form a first reaction effluent containing ethylene glycol. The first reaction effluent, the second solvent stream and the second hydrogen stream were fed to the second reactor to contact with the copper-containing catalyst II, to form a second reaction effluent containing ethylene glycol. The first reactor was operated under the following conditions: a reaction temperature of 180° C., a WHSV of 1 $hr^{-1}$, and a reaction pressure of 1.5 MPa; and the second reactor was operated under the following conditions: a reaction temperature of 230° C., a WHSV of 0.9 $hr^{-1}$, and a reaction pressure of 1.8 MPa. Reaction results were obtained as follows: conversion of the diethyl oxalate was 100%, and selectivity for ethylene glycol was 91.8%.

Example 10

$CuO$—$Cu/Al_2O_3$ catalyst I having a composition of 45% $CuO$+5% $Cu/Al_2O_3$ and $Cu_2O$—$Cu/SiO_2$ catalyst II having a composition of 10% $Cu_2O$+20% $Cu/SiO_2$ were prepared according to a procedure similar to that described in Example 7.

This example used diethyl oxalate and hydrogen as feedstock, and propanol as solvent, wherein the molar ratio of the diethyl oxalate to the hydrogen to the solvent was 1:60:0.2, the hydrogen feedstock was split into a first hydrogen stream and a second hydrogen stream in a molar ratio of 4.5:1, and the propanol solvent was split into a first solvent stream and a second solvent stream in a molar ratio of 4:1. The diethyl oxalate, the first hydrogen stream and the first solvent stream were fed to the first reactor to contact with the copper-containing catalyst I, to form a first reaction effluent containing ethylene glycol. The first reaction effluent, the second solvent stream and the second hydrogen stream were fed to the second reactor to contact with the copper-containing catalyst II, to form a second reaction effluent containing ethylene glycol. The first reactor was operated under the following conditions: a reaction temperature of 200° C., a WHSV of 3 $hr^{-1}$, and a reaction pressure of 2.2 MPa; and the second reactor was operated under the following conditions: a reaction temperature of 240° C., a WHSV of 2.5 $hr^{-1}$, and a reaction pressure of 2.2 MPa. Reaction results were obtained as follows: conversion of the diethyl oxalate was 100%, and selectivity for ethylene glycol was 90.7%.

Example 11

$CuO$—$Cu$—$MnO$—$ZnO/SiO_2$ catalyst I having a composition of 40% $CuO$+5% $Cu$+0.5% $MnO$+1% $ZnO/SiO_2$ and Cu₂O/SiO₂ catalyst II having a composition of 30% Cu₂O/SiO₂ were prepared according to a procedure similar to that described in Example 7.

This example used diethyl oxalate and hydrogen as feedstock, and ethanol as solvent, wherein the molar ratio of the diethyl oxalate to the hydrogen to the solvent was 1:120:0.8, the hydrogen feedstock was split into a first hydrogen stream and a second hydrogen stream in a molar ratio of 5:1, and the ethanol solvent was split into a first solvent stream and a second solvent stream in a molar ratio of 6:1. The diethyl oxalate, the first hydrogen stream and the first solvent stream were fed to the first reactor to contact with the copper-containing catalyst I, to form a first reaction effluent containing ethylene glycol. The first reaction effluent, the second solvent stream and the second hydrogen stream were fed to the second reactor to contact with the copper-containing catalyst II, to form a second reaction effluent containing ethylene glycol. The first reactor was operated under the following conditions: a reaction temperature of 210° C., a WHSV of 5 hr⁻¹, and a reaction pressure of 3.5 MPa; and the second reactor was operated under the following conditions: a reaction temperature of 250° C., a WHSV of 5 hr⁻¹, and a reaction pressure of 3.5 MPa. Reaction results were obtained as follows: conversion of the diethyl oxalate was 100%, and selectivity for ethylene glycol was 95.8%.

Example 12

CuO—MnO/Al₂O₃ catalyst I having a composition of 25% CuO+0.8% MnO/Al₂O₃ and Cu₂O/SiO₂ catalyst II having a composition of 5% Cu₂O/SiO₂ were prepared according to a procedure similar to that described in Example 7.

This example used dimethyl oxalate and hydrogen as feedstock, and methanol as solvent, wherein the molar ratio of the dimethyl oxalate to the hydrogen to the solvent was 1:60:4, the hydrogen feedstock was split into a first hydrogen stream and a second hydrogen stream in a molar ratio of 8:1, and the methanol solvent was split into a first solvent stream and a second solvent stream in a molar ratio is 8:1. The dimethyl oxalate, the first hydrogen stream and the first solvent stream were fed to the first reactor to contact with the copper-containing catalyst I, to form a first reaction effluent containing ethylene glycol. The first reaction effluent, the second solvent stream and the second hydrogen stream were fed to the second reactor to contact with the copper-containing catalyst II, to form a second reaction effluent containing ethylene glycol. The first reactor was operated under the following conditions: a reaction temperature of 230° C., a WHSV of 0.7 hr⁻¹, and a reaction pressure of 6 MPa; and the second reactor was operated under the following conditions: a reaction temperature of 260° C., a WHSV of 3 hr⁻¹, and a reaction pressure of 6 MPa. Reaction results were obtained as follows: conversion of dimethyl oxalate was 99.8%, and selectivity for ethylene glycol was 95.2%.

Example 13

CuO/SiO₂ catalyst I having a composition of 35% CuO/SiO₂, CuO/SiO₂ catalyst II having a composition of 50% CuO/SiO₂, and Cu₂O/SiO₂ catalyst III having a composition of 40% Cu₂O/SiO₂ were prepared according to a procedure similar to that described in Example 7.

This example used dimethyl oxalate and hydrogen as feedstock, and methanol as solvent, wherein the molar ratio of the dimethyl oxalate to the hydrogen to the solvent was 1:120:1, the hydrogen feedstock was split into a first hydrogen stream, a second hydrogen stream and a third hydrogen stream in a molar ratio of 1:1:1, and the methanol solvent was split into a first solvent stream, a second solvent stream and a third solvent stream in a molar ratio of 1:1:2. The dimethyl oxalate, the first hydrogen stream and the first solvent stream were fed to the first reactor to contact with the copper-containing catalyst I, to form a first reaction effluent containing ethylene glycol. The first reaction effluent, the second solvent stream and the second hydrogen stream were fed to the second reactor to contact with the copper-containing catalyst II, to form a second reaction effluent containing ethylene glycol. The second reaction effluent, the third solvent stream and the third hydrogen stream were fed to the third reactor to contact with the copper-containing catalyst III, to form a third reaction effluent containing ethylene glycol. The first reactor was operated under the following conditions: a reaction temperature of 180° C., a WHSV of 0.5 hr⁻¹, and a reaction pressure of 3.5 MPa; the second reactor was operated under the following conditions: a reaction temperature of 230° C., a WHSV of 0.2 hr⁻¹, and a reaction pressure of 3.5 MPa; and the third reactor was operated under the following conditions: a reaction temperature of 250° C., a WHSV of 0.4 hr⁻¹, and a reaction pressure is 3.5 MPa. Reaction results were obtained as follows: conversion of dimethyl oxalate was 100%, and selectivity for ethylene glycol was 96.0%.

Comparative Example 2

CuO—Cu/Al₂O₃ catalyst having a composition of 45% CuO+5% Cu/Al₂O₃ was prepared according to a procedure similar to that described in Example 7.

This example used diethyl oxalate and hydrogen as feedstock, and propanol as solvent, wherein the molar ratio of the diethyl oxalate to the hydrogen to the solvent was 1:60:0.2. The diethyl oxalate, the hydrogen and the solvent were fed to the reactor containing the copper-containing catalyst I to contact with the catalyst, to form a reaction effluent containing ethylene glycol. The reactor was operated under the following conditions: a reaction temperature of 200° C., a WHSV of 1.36 hr⁻¹, and a reaction pressure of 2.2 MPa.

Comparison of the reaction results obtained in Example 10 and Comparative Example 2 is shown in Table 2 below.

TABLE 2

Comparison of reaction results obtained in two-reactors-in-series process (as described herein) and in one-stage-reactor process

| | Two-reactors-in-series process (Example 10) | | | One-stage reactor process (Comp. Example 2) | |
|---|---|---|---|---|---|
| Time, hours | Oxalate conversion, % | Selectivity for ethylene glycol, % | Time, hours | Oxalate conversion, % | Selectivity for ethylene glycol, % |
| 6 | 100.00 | 90.00 | 6.2 | 85.50 | 50.00 |
| 10 | 100.00 | 86.00 | 10.5 | 98.77 | 80.50 |
| 20 | 100.00 | 93.30 | 20.3 | 98.70 | 80.32 |
| 29.5 | 100.00 | 90.71 | 30 | 98.46 | 78.76 |
| 42.5 | 100.00 | 90.33 | 42 | 90.00 | 77.00 |
| 50 | 98.46 | 91.39 | 50.8 | 75.00 | 67.00 |
| 54 | 100.00 | 90.77 | 54.9 | 60.00 | 65.00 |
| 58 | 100.00 | 90.11 | 58.8 | 50.00 | 50.00 |
| 101.5 | 100.00 | 91.06 | | | |
| 260.5 | 100.00 | 89.14 | | | |
| 352 | 100.00 | 89.67 | | | |
| 550 | 100.00 | 87.81 | | | |
| 780 | 100.00 | 89.73 | | | |

From the data shown in the above table, it can be seen that is the processes described herein are superior to the conventional technical solution with respect to the conversion of the feedstock, the selectivity for the product, and the stability of the catalyst.

While the invention has been described with reference to exemplary embodiments, it will be understood by those skilled in the art that various changes and modifications may be made without departing from the spirit and scope of the invention. Therefore, the invention is not limited to the embodiments disclosed, but the invention will include all embodiments falling within the scope of the appended claims.

What is claimed is:

1. A process for producing ethylene glycol from oxalate(s), comprising:
   a) feeding hydrogen and a first oxalate stream to a first reaction zone to contact them with a first copper-containing catalyst under hydrogenation conditions, to form a first reaction effluent containing ethylene glycol;
   b) feeding the first reaction effluent and a second oxalate stream to a second reaction zone to contact them with a second copper-containing catalyst under hydrogenation conditions, to form a second reaction effluent containing ethylene glycol; and
   c) isolating ethylene glycol from the second reaction effluent;
   wherein the molar ratio of the oxalate(s) in the first oxalate stream to the oxalate in the second oxalate stream ranges from 0.1:1 to 10:1, and wherein the molar ratio of the hydrogen to the total oxalate(s) in the first and the second oxalate streams ranges from 20:1 to 300:1.

2. The process of claim 1, wherein the first oxalate stream and the second oxalate stream are independently selected from dimethyl oxalate, diethyl oxalate, dipropyl oxalate, diisopropyl oxalate, and mixtures thereof.

3. The process of claim 1, wherein the molar ratio of the oxalate(s) in the first oxalate stream to the oxalate(s) in the second oxalate stream ranges from 0.2:1 to 8:1.

4. The process of claim 1, wherein the first reaction zone is operated under the following conditions:
   a reaction temperature ranging from 100 to 260° C., a WHSV ranging from 0.05 to 10 $h^{-1}$, and a reaction pressure ranging from 0.2 to 5.0 MPa; and
   the second reaction zone is operated under the following conditions: a reaction temperature ranging from 180 to 300° C., a WHSV ranging from 0.08 to 8 $h^{-1}$, and a reaction pressure ranging from 1.0 to 10.0 MPa.

5. The process of claim 4, wherein
   the first reaction zone is operated under the following conditions: a reaction temperature ranging from 130 to 230° C., a WHSV ranging from 0.08 to 6 $h^{-1}$, and a reaction pressure ranging from 0.5 to 3.0 MPa; and
   the second reaction zone is operated under the following conditions: a reaction temperature ranging from 180 to 260° C., a WHSV ranging from 0.1 to 5 $h^{-1}$, and a reaction pressure ranging from 1.5 to 6.0 MPa.

6. The process of claim 1, wherein the first copper-containing catalyst and the second copper-containing catalyst are the same or different, and comprise an active component, a carrier and an optional assistant,
   wherein the carrier comprises silica, alumina, or both;
   the active component is selected from copper element, oxides of copper, and mixtures thereof, and the content of the active component ranges from 0.02 to 60 wt % based on the weight of the respective catalyst;
   the optional assistant comprises at least one metal selected from zinc, manganese, barium, chromium, nickel and iron, or oxides thereof, and the content of the assistant ranges from 0 to 30 wt % based on the weight of the respective catalyst.

7. The process of claim 6, wherein the content of the active component ranges from 0.1 to 50 wt %, and the content of the optional assistant ranges from 0.5 to 20 wt %, based on the weight of the respective catalyst.

8. The process of claim 1, further comprising feeding a solvent to the first and/or the second reaction zone, wherein the solvent is selected from $C_1$ to $C_5$ alcohols, $C_2$ to $C_{10}$ ethers, $C_5$ to $C_{10}$ alkanes, $C_5$ to $C_{10}$ cycloalkanes, $C_6$ to $C_{10}$ aromatic hydrocarbons, and mixtures thereof, and wherein the molar ratio of the solvent to the total oxalate(s) ranges from 0.1:1 to 5:1.

9. The process of claim 1, wherein the reaction temperature in the second reaction zone is higher than the reaction temperature in the first reaction zone by at least 10° C.

10. A process for producing ethylene glycol from oxalate(s), comprising:
   a) feeding oxalate(s), a first solvent stream and a first hydrogen stream to a first reaction zone to contact them with a first copper-containing catalyst, to form a first reaction effluent containing ethylene glycol;
   b) feeding the first reaction effluent, a second hydrogen stream and optionally a second solvent stream to a second reaction zone to contact them with a second copper-containing catalyst, to form a second reaction effluent containing ethylene glycol; and
   c) isolating ethylene glycol from the second reaction effluent;
   wherein, the first and the second solvent streams are independently selected from $C_1$ to $C_5$ alcohols, $C_2$ to $C_{10}$ ethers, $C_5$ to $C_{10}$ alkanes, $C_5$ to $C_{10}$ cycloalkanes, $C_6$ to $C_{10}$ aromatic hydrocarbons, and mixtures thereof; the molar ratio of the first solvent stream to the second solvent stream is at least 0.1:1; the molar ratio of the first hydrogen stream to the second hydrogen stream ranges from 0.2:1 to 10:1; and the molar ratio of the oxalate(s) to the total hydrogen in the first and the second hydrogen streams to the total solvent in the first and the second solvent streams is 1:30 to 200:0.1 to 5.

11. The process of claim 10, wherein the oxalate(s) is selected from dimethyl oxalate, diethyl oxalate, dipropyl oxalate, diisopropyl oxalate, and mixtures thereof.

12. The process of claim 10, wherein the first and the second solvent streams are independently selected from methanol, ethanol, propanol, cyclohexane, and mixtures thereof.

13. The process of claim 10, wherein the molar ratio of the first solvent stream to the second solvent stream ranges from 0.1:1 to 10:1.

14. The process of claim 10, wherein the molar ratio of the first hydrogen stream to the second hydrogen stream ranges from 0.3:1 to 8:1.

15. The process of claim 10, wherein
   the first reaction zone is operated under the following conditions: a reaction temperature ranging from 100 to 260° C., a WHSV ranging from 0.05 to 10 $h^{-1}$, a reaction pressure ranging from 0.2 to 5.0 MPa, and a mass fraction of the oxalate(s) ranging from 0.5 to 95%; and
   the second reaction zone is operated under the following conditions: a reaction temperature ranging from 180 to 300° C., a WHSV ranging from 0.08 to 8 $h^{-1}$, and a reaction pressure ranging from 1.0 to 10.0 MPa.

16. The process of claim 15, wherein
   the first reaction zone is operated under the following conditions: a reaction temperature ranging from 130 to 230°

C., a WHSV ranging from 0.08 to 6 h$^{-1}$, a reaction pressure ranging from 0.5 to 4.0 MPa, and a mass fraction ranging the oxalate(s) ranging from 1.0 to 60%; and the second reaction zone is operated under the following conditions: a reaction temperature ranging from 180 to 260° C., a WHSV ranging from 0.1 to 5 h$^{-1}$, and a reaction pressure ranging from 1.5 to 6.0 MPa.

17. The process of claim 10, wherein the first copper-containing catalyst and the second copper-containing catalyst are the same or different, and comprise an active component, a carrier and an optional assistant, wherein the carrier comprises silica, alumina, or both;

the active component is selected from copper element, oxides of copper, and mixtures thereof, and the content the active component ranges from 0.02 to 60 wt % based on the weight of the respective catalyst;

the assistant comprises at least one metal selected from zinc, manganese, barium, chromium, nickel and iron, or oxides thereof, and the content the assistant ranges from 0 to 30 wt % based on the weight of the respective catalyst.

18. The process of claim 17, wherein the content of the active component ranges from 0.1 to 50 wt %, and the content of the assistant ranges from 0.5 to 20 wt %, based on the weight of the respective catalyst.

19. The process of claim 10, wherein the reaction temperature in the second reaction zone is higher than the reaction temperature in the first reaction zone by at least 10° C.

* * * * *